United States Patent [19]
Ahrndt et al.

[11] Patent Number: 5,958,951
[45] Date of Patent: Sep. 28, 1999

[54] MODIFIED FORM OF THE R(−)-N-(4,4-DI(3-METHYLTHIEN-2-YL)BUT-3-ENYL)-NIPECOTIC ACID HYDROCHLORIDE

[75] Inventors: Preben Ahrndt, Ølstykke; Henning Børge Petersen, Lyngby, both of Denmark; Vincent H. Chang, Lake Forest, Ill.; Kimberly Ann Allen, Silver Lake, Wis.; Michael H. Cain, Grayslake, Ill.

[73] Assignee: Novo Nordiskials, Bagsvoerd, Denmark

[21] Appl. No.: 08/872,380

[22] Filed: Jun. 10, 1997

Related U.S. Application Data

[60] Provisional application No. 60/020,978, Jun. 24, 1996.

[30] Foreign Application Priority Data

Jun. 14, 1996 [DK] Denmark ................................. 0661/96

[51] Int. Cl.$^6$ ........................ A61K 31/445; C07D 409/14
[52] U.S. Cl. ............................................ 514/326; 546/212
[58] Field of Search .............................. 514/326; 546/212

[56] References Cited

U.S. PATENT DOCUMENTS 5,010,090  4/1991  Gronvald et al. ........................ 514/326

OTHER PUBLICATIONS

McGraw et al. "The identification and characterization of polymorphism in tiagabine HCl bulk drug" Derwent abst 95–05633, 1994.

Andersen et al., J. Med. Chem., vol. 36, pp. 1716–1725 (1993).

*Primary Examiner*—Ceila Chang
*Attorney, Agent, or Firm*—Steve T. Zelson; Carol E. Rozek

[57] ABSTRACT

The present invention provides R(−)-N-(4,4-di(3-methylthien-2-yl)but-3-enyl)-nipecotic acid hydrochloride in its pure and stable anhydrous form.

7 Claims, 8 Drawing Sheets

MODIFIED FORM OF THE R(−)-N-(4,4-DI(3-METHYLTHIEN-2-YL)BUT-3-ENYL)-NIPECOTIC ACID HYDROCHLORIDE

CROSS-REFERENCE TO RELATED APPLICATIONS

This application claims priority under 35 U.S.C. 119 of Danish application Ser. No. 0661/96 filed Jun. 14, 1996 and U.S. provisional application No. 60/020,978 filed Jun. 24, 1996, the contents of which are fully incorporated herein by reference.

The present invention relates to the anhydrous crystalline form of the R(−)-N-(4,4-di(3-methylthien-2-yl)but-3-enyl)-nipecotic acid hydrochloride its preparation and use as therapeutic agent.

U.S. Pat. No. 5,010,090 discloses a class of novel compounds that exhibit gamma-amino butyric acid uptake (referred to as GABA uptake) inhibitory properties and therefore said compounds are valuable for therapeutic use in the treatment of epilepsy and other diseases related to GABA uptake.

In the present invention the R(−)-N-(4,4-di(3-methylthien-2-yl)but-3-enyl)-nipecotic acid is referred to by its generic name of Tiagabine (INN).

In U.S. Pat. No. 5,354,760 Tiagabine hydrochloride is disclosed in its monohydrate form.

Method for transdermal delivery of N-(4,4-di(3-methylthien-2-yl)-but-3-enyl)-nipecotic acid and pharmaceutically acceptable derivatives thereof is disclosed in WO 95/31976.

However, the monohydrate, which is stable at normal room temperature under dry and dark conditions, has shown less stability at elevated temperatures. The monohydrate will give off water at higher temperatures starting at about 50° C. and resulting in a total loss of all water at the melting point at 80–85° C. The features of the monohydrate is very inconvenient in the formulation work with the compound. The alternative product, which is described in the U.S. Pat. No. 5,010,090 (column 8, line 62) can only be prepared through a labour intensive process as described, using ethyl acetate.

Furthermore analysis has shown that products manufactured by this process contain unwanted amounts of the crystallizing solvent.

Other organic solvents may be used in the isolation of the product, but organic solvents will often form chlathrates, i.e. solvates of tiagabine hydrochloride and the resp. organic solvent.

These solvents are unwanted because they are either toxic to humans or may give rises to interaction-reactions with other ingredients in the pharmaceutical preparation, resulting in low stability of the dosage form.

Further it has been found that the compound is heavily soluble in the applied organic solvents, which is very inconvenient when working on larger scale.

It has now been found that an anhydrate form can be obtained from water solutions under special conditions, which allow the anhydrate to be formed selectively and in high purity and recovery.

The anhydrate form of Tiagabine hydrochloride is non-hygroscopic and thermally stable under normal storage conditions.

The anhydrous form of the present invention is very applicable for the pharmaceutical formulation and stable under the normal process conditions used.

The Tiagabine hydrochloride anhydrate is characterized by a specific X-ray powder diffractogram and a typical IR-spectrum of the crystals in KBr. As shown in FIG. 2, the X-ray powder diffraction pattern exhibits the following main peaks: 6.4, 11.3, 13.0, 13.9, 15.0, 18.7, 19.4, 22.5 and 23.7. The Differential Scanning Calorimetry (DSC) profile of the anhydrate is typical of showing only 1 peak indicating the melting of the compound at temperatures from 190 to 200° C.

The present invention also provides a process for producing the crystalline anhydrous Tiagabine hydrochloride, which comprises crystallizing Tiagabine hydrochloride from an aqueous hydrochloric acid solution in not less than 0.55 M hydrochloric acid concentration, preferably in not less than 1.3 M hydrochloric acid concentration.

The solution of Tiagabine and hydrochloride is normally made up at a temperature above 50° C.

The crystallization may be initiated by seeding, but this can also be omitted as the crystallization can start spontaneously.

The crystals can be isolated by conventional procedures such as filtration or centrifugation. The crystals may be rinsed by water or diluted hydrochloric acid before drying, which can be performed either under reduced pressure or at normal pressure at room temperature or higher temperatures.

It has now been found that the anhydrate form of N-(4,4-di(3-methylthien-2-yl)-but-3-enyl)-nipecotic acid hydrochloride obtained as described in the present invention will solve the problems related to the monohydrate-form in the manufacture of the medicinal product. The present invention also provides pharmaceutical compositions comprising the anhydrous crystalline form of the R(−)-N-(4,4-di(3-methylthien-2-yl)but-3-enyl)-nipecotic acid hydrochloride and a pharmaceutically acceptable carrier.

The compositions of this invention are usually adapted for oral administration, but formulations for dissolution for parenteral administration, transdermal delivery or sustained release delivery are also within the scope of this invention.

The composition is usually presented as a unit dose composition containing 0.1–3000 mg of a compound in accordance with the invention for oral dosing. Typical dosage for the treatment of epilepsy would vary between 1.0–500 mg, preferably between 1–1000 mg per day and more preferably between 1 to 100 mg per day either once or divided in 2 or 3 doses when administered orally.

Preferred unit dosage forms include in solid form, tablets or capsules, in liquid form, solutions, suspensions, emulsions, elixirs or capsules filled with the same, in the form of patches for transdermal administration or in form of sterile injectable solutions.

The composition of this invention may be formulated by conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxy ethoxylated castor oil, syrup, peanut oil, olive oil, gelatin, lactose, terra alba, sucrose, agar, pectin, acacia, amylose, magnesium stearate, talc, silicic acid, stearic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as binders, lubricants, preservatives, disintegrants, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

For oral administration, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed.

A typical tablet, which may be prepared by conventional tabletting techniques, contains:

| Tablet Strenghts, mg | 8 |
|---|---|
| Tablet Gross Mass, mg | 320 |
| Tiagabine Hydrochloride Anhydrate | 8.35 |
| Polyethylene Glycol 6000, NF | 16.0 |
| Lactose, anhydrous, NF | 279 |
| δ-Tocopherol, Ph.Eur. | 0.800 |
| Talc, Ph.Eur. | 16.0 |

The invention also provides methods of treatment of diseases related to GABA uptake in mammals including humans which methods comprises administering an effective amount of an anhydrous crystalline form of the R(−)-N-(4,4-di(3-methylthien-2-yl)but-3-enyl)-nipecotic acid hydrochloride.

The invention further provides a pharmaceutically acceptable anhydrous crystalline form of the R(−)-N-(4,4-di(3-methylthien-2-yl)but-3-enyl)-nipecotic acid hydrochloride for therapeutic use in the treatment of epilepsy and other diseases related to GABA uptake.

EXAMPLE 1

Tiagabine, hydrochloride (anhydrous)

Figure 1:
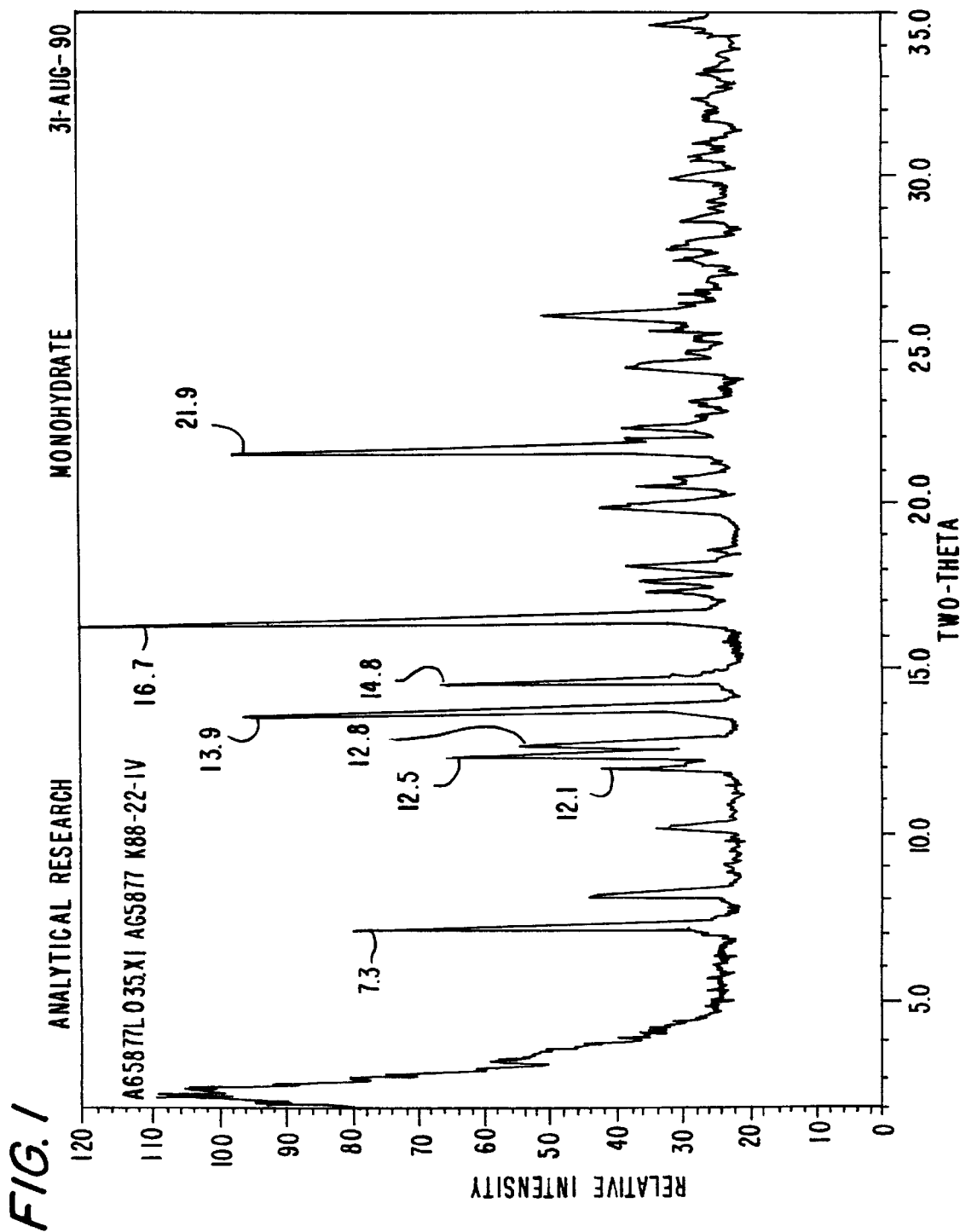
FIG. 1 is an X-ray powder diffractogram of Tiagabine hydrochloride monohydrate.
Figure 2:
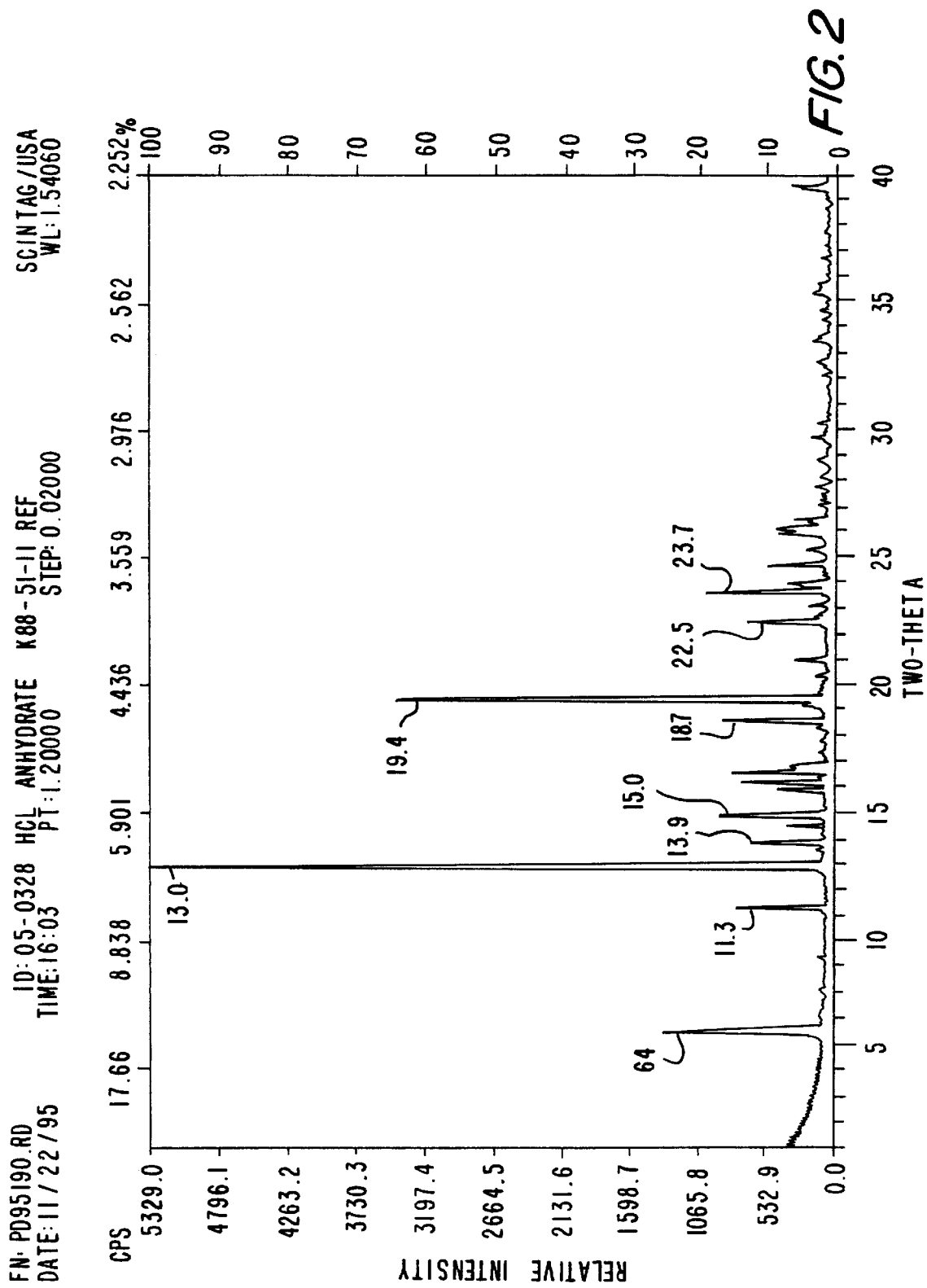
FIG. 2 is an X-ray powder diffractogram of Tiagabine hydrochloride anhydrate.
Figure 3:
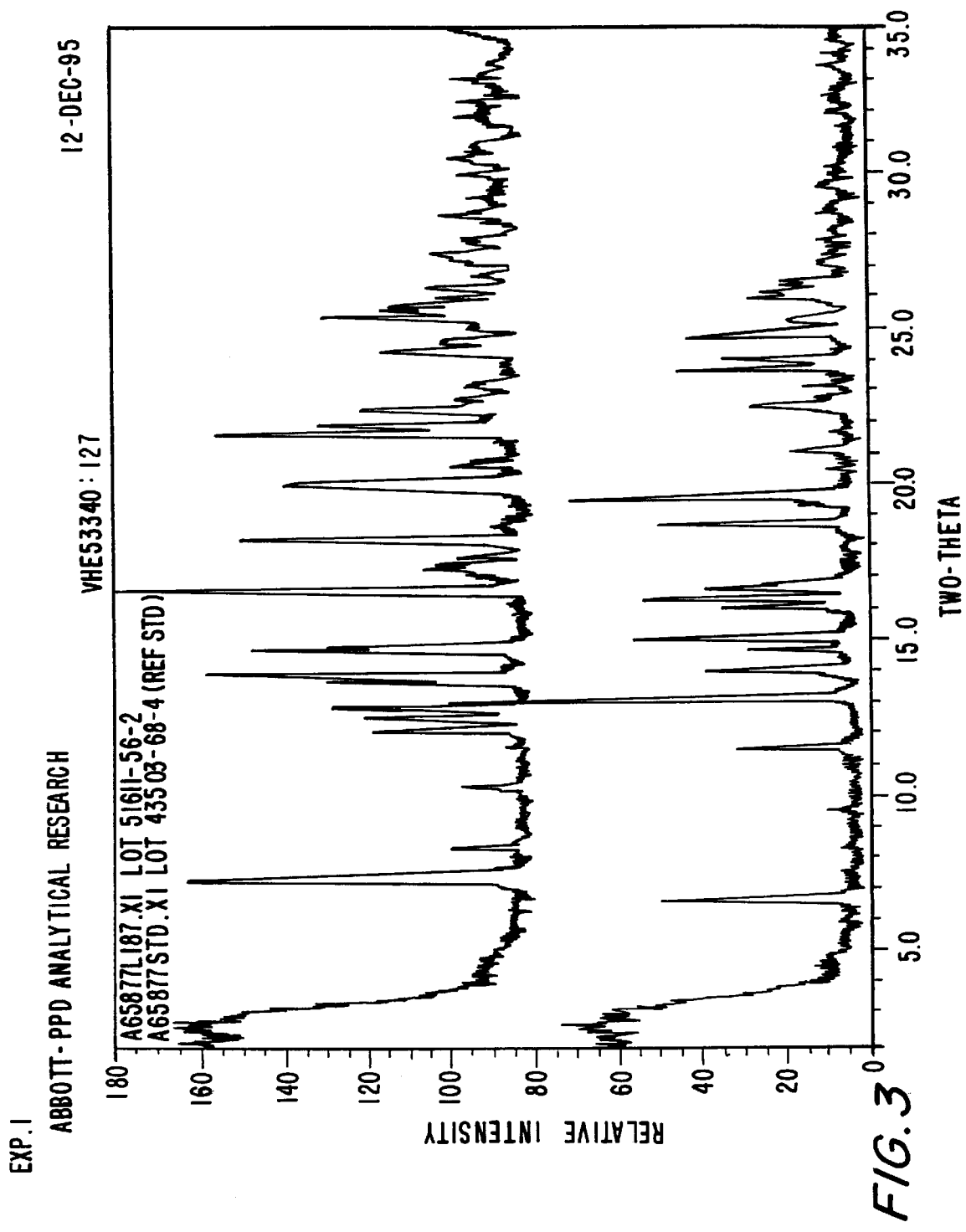
FIG. 3 shows the X-ray powder diffractogram of Tiagabine hydrochloride anhydrate as prepared in Example 1 (bottom) compared with the X-ray powder diffractogram of Tiagabine hydrochloride monohydrate (top).
Figure 4:
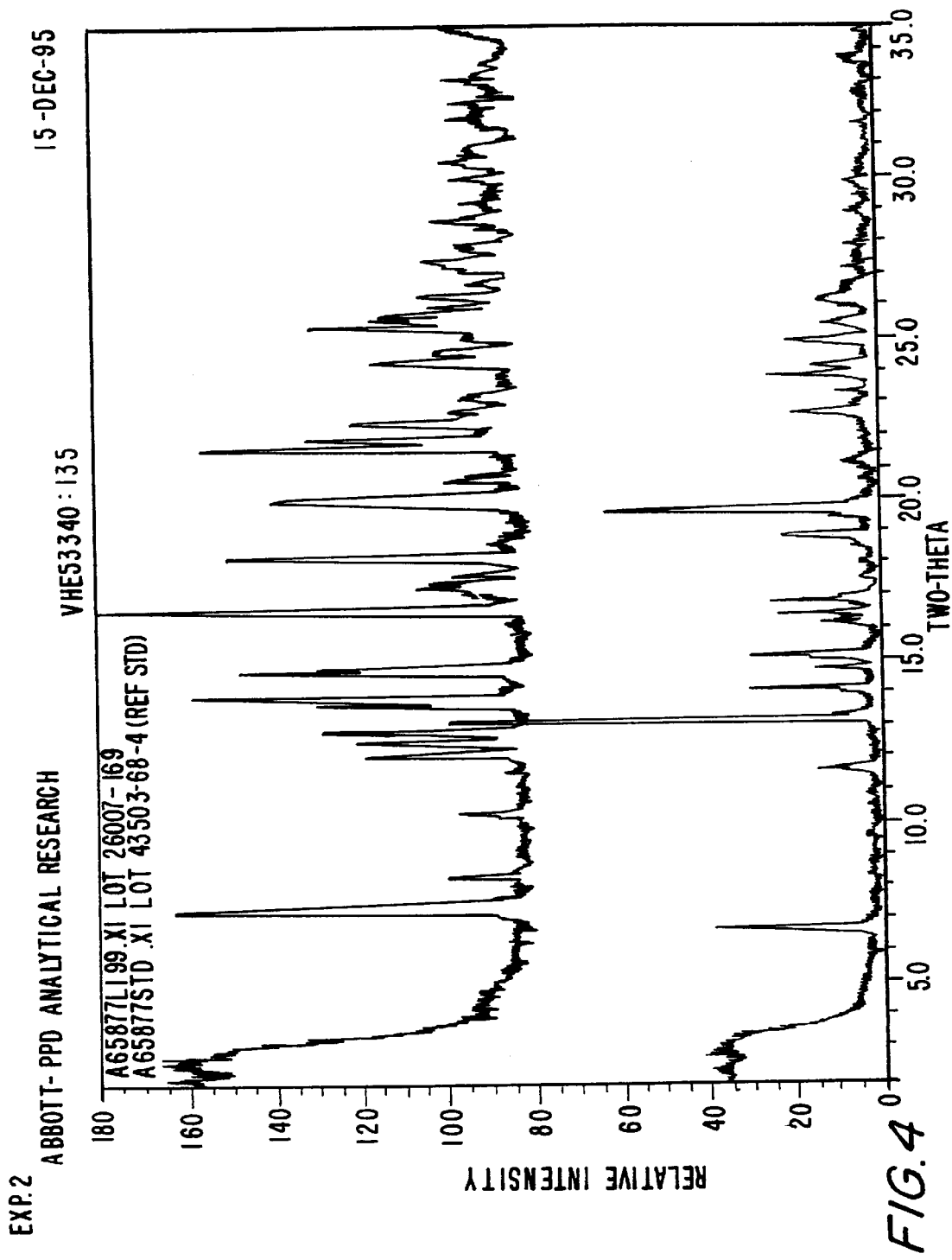
FIG. 4 shows the X-ray powder diffractogram of Tiagabine hydrochloride anhydrate as prepared in Example 2 (bottom) compared with the X-ray powder diffractogram of Tiagabine hydrochloride monohydrate (top).
Figure 5:
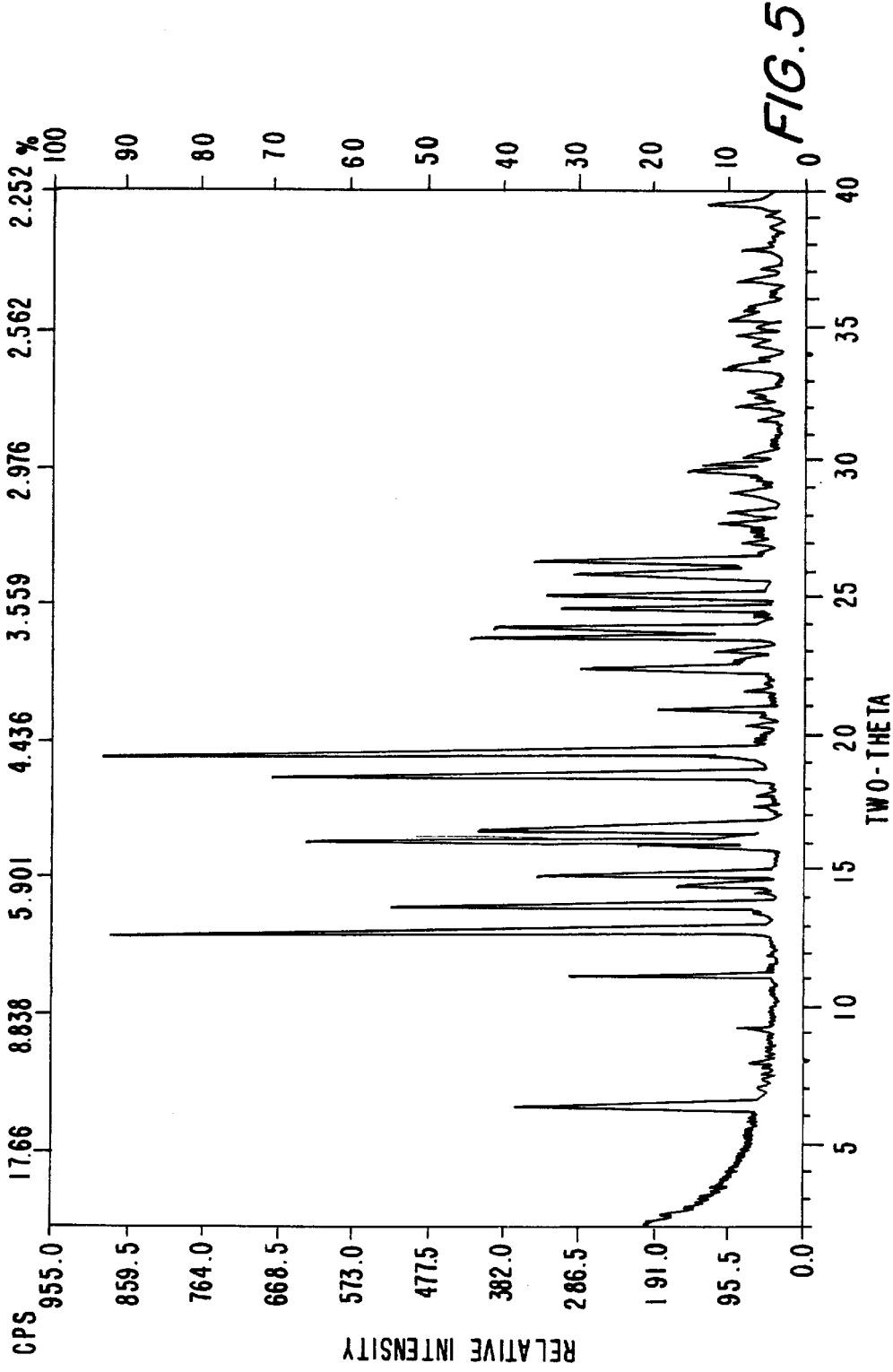
FIG. 5 is an X-ray powder diffractogram of Tiagabine hydrochloride anhydrate as prepared in Example 3.
Figure 6:
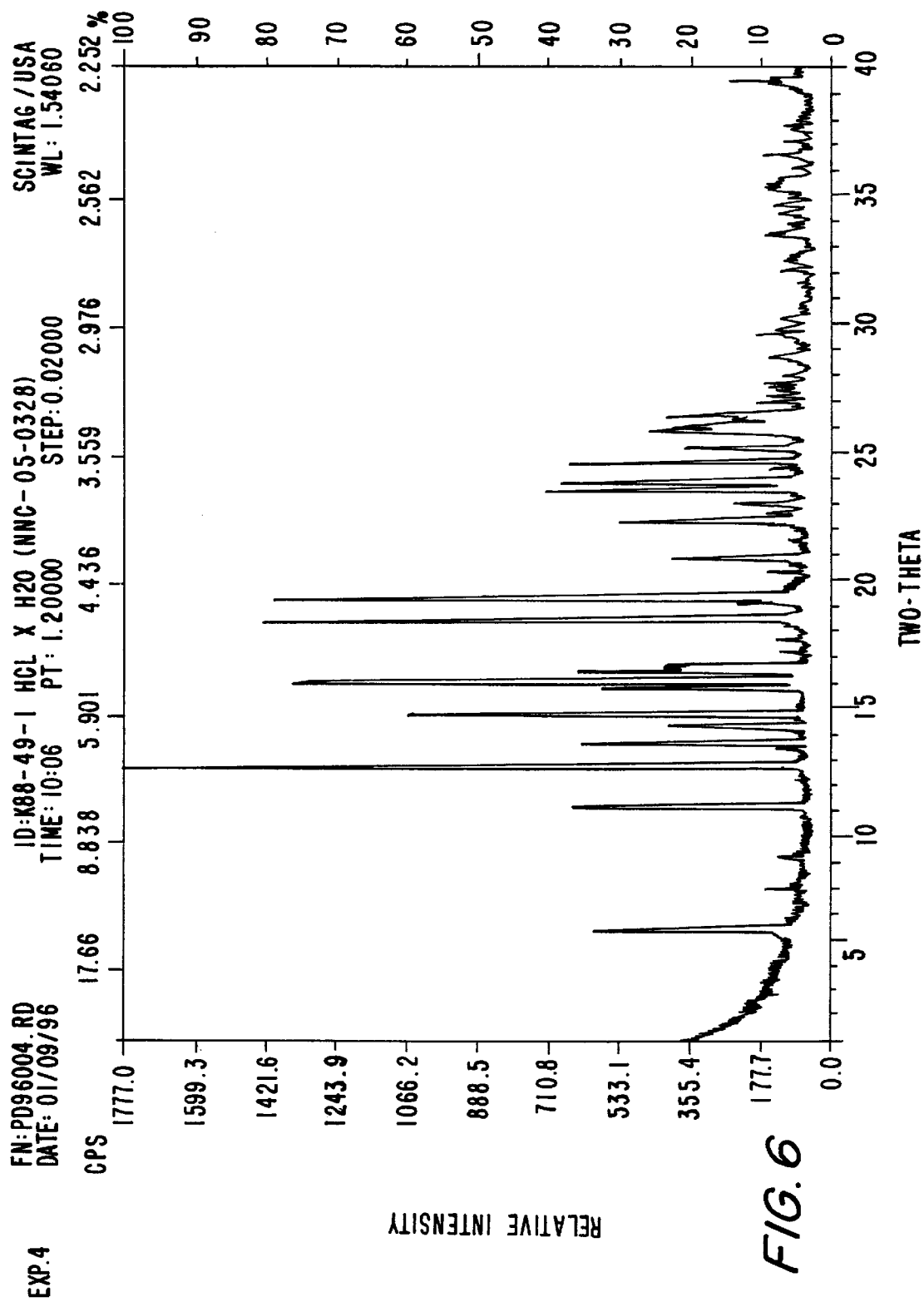
FIG. 6 is an X-ray powder diffractogram of Tiagabine hydrochloride anhydrate as prepared in Example 4.
Figure 7:
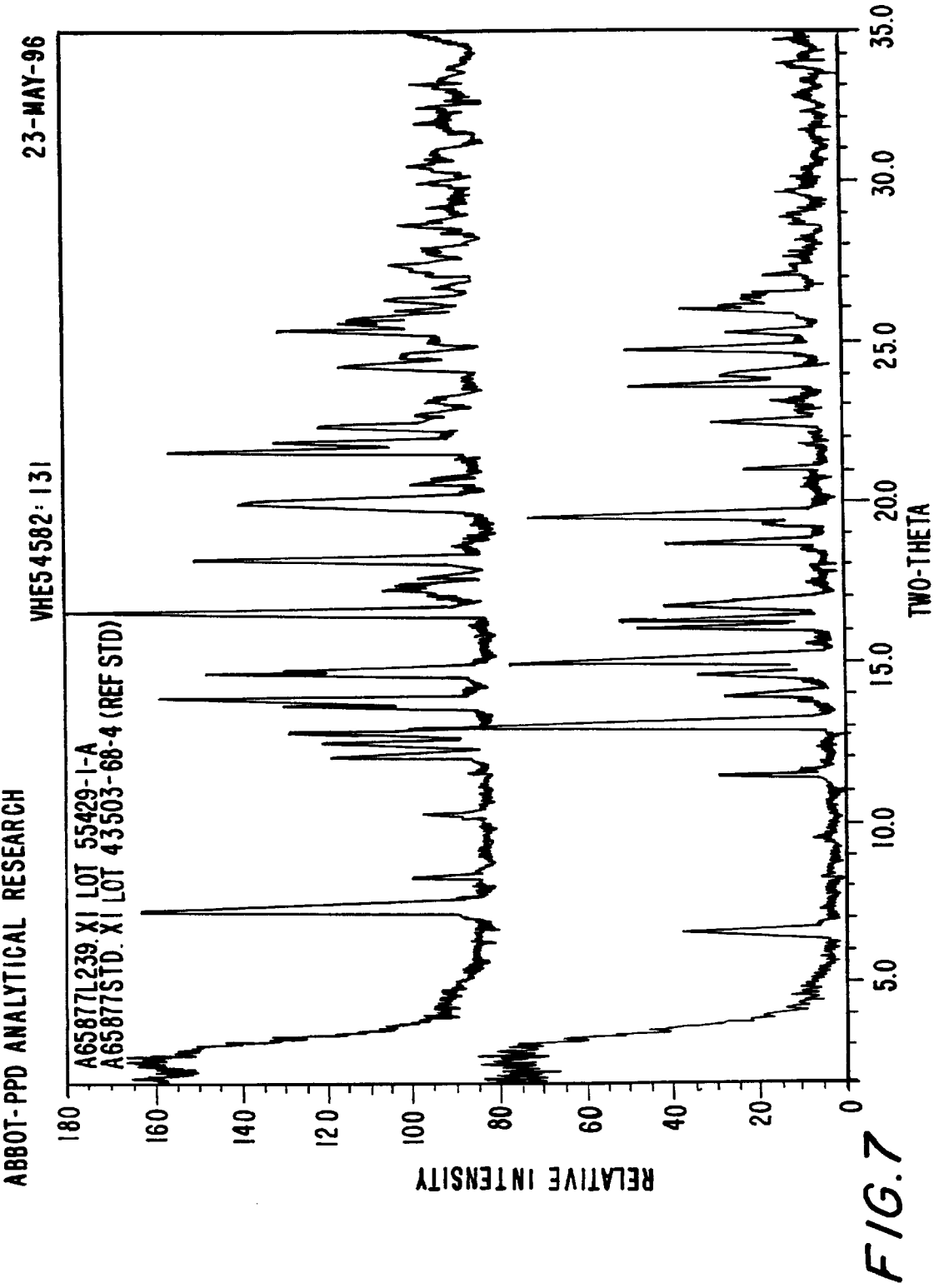
FIG. 7 shows the X-ray powder diffractogram of Tiagabine hydrochloride anhydrate as prepared in Example 5 (bottom) compared with the X-ray powder diffractogram of Tiagabine hydrochloride monohydrate (top).
Figure 8:
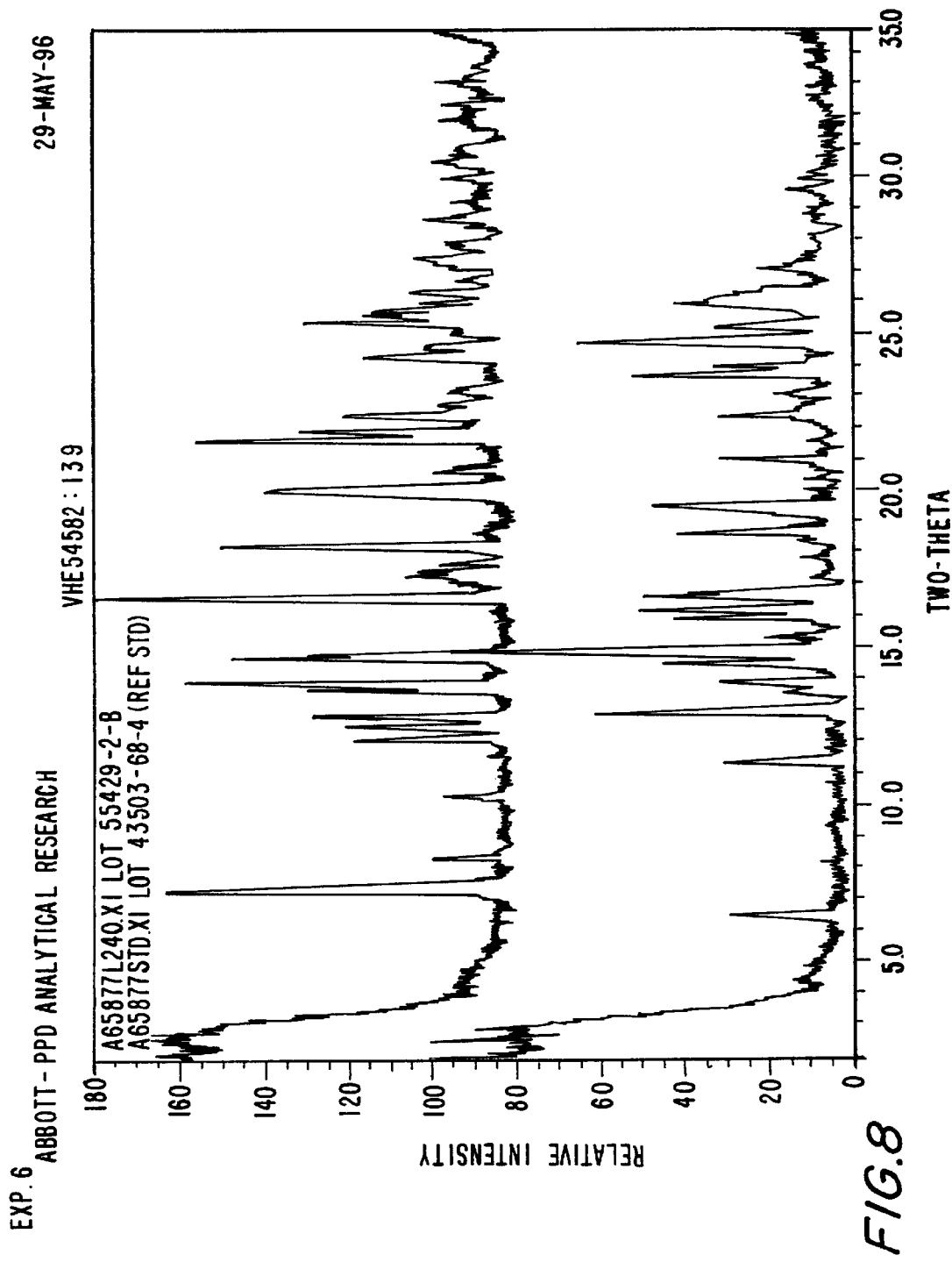
FIG. 8 shows the X-ray powder diffractogram of Tiagabine hydrochloride anhydrate as prepared in Example 6 (bottom) compared with the X-ray powder diffractogram of Tiagabine hydrochloride monohydrate (top).

100 g of Tiagabine, hydrochloride monohydrate was dissolved in 700 ml of 0.2 N hydrochloric acid at 55° C. The concentration of hydrochloric acid, was adjusted to 1.3 N by addition of conc. hydrochloric acid. The crystallization of the product started spontaneous during addition of the acid. Stirring is continued at 50° C. for 17 hrs. The product was filtered off and dried under vacuum giving 95% of tiagabine, hydrochloride.

Karl Fisher (K.F.): <1% water.

X-Ray: Complies with the anhydrous crystal form.

EXAMPLE 2

Tiagabine, hydrochloride (anhydrous)

Tiagabine hydrochloride was dissolved in 7 ml of 0.25 N HCl pr. gram of tiagabine at 55° C. The solution was adjusted to 0.8 N with conc. hydrochloric acid. Then 0.5 g/l of seed crystals were charged to the solution, which was stirred at 52° C. for 18 hrs. The product was filtered off and dried at room temperature, giving 85% in yield.

X-Ray complies with the anhydrous crystal form.

EXAMPLE 3

Tiagabine, hydrochloride (anhydrous)

75 g Tiagabine hydrochloride monohydrate was dissolved in 613 ml of water at 65° C. The solution was filtered and 37 g of conc. hydrochloric acid diluted in 115 g of water was added.

The solution was cooled to 52° C. and stirred overnight.

The suspension was cooled to 40° C. before filtering off the product. The filter cake was rinsed with 2 times 55 g of water before drying in vacuum at 30° C.

K.F.: 0% water.

X-Ray: Complies with the anhydrous crystal form.

DSC: onset 193° C.

HPLC: 99.9% purity.

EXAMPLE 4

Tiaaabine, hydrochloride (anhydrous)

10 g of Tiagabine, hydrochloride monohydrate was stirred with 100 ml 1N hydrochloric acid at 70° C.

The mixture was cooled to room temperature and stirred overnight giving a suspension of fine crystals.

The product was filtered off and washed with water before drying in vacuum at 40° C.

Yield: 9 g$^{118}$ 95%

HPLC purity: 99.9%

DSC (Onset): 197.8° C.

Thermal Gravimetric Analysis (TGA): 0.15% weightless to 160° C.

X-Ray: Complies with the anhydrous crystal form.

EXAMPLE 5

Tiagabine. hydrochloride (anhvdrous)

To a 1 L flask, 50 g of tiagabine ethyl ester, 750 ml of water and 11 g of conc. hydrochloric acid were charged. The mixture was heated to reflux for 2 hours and then ethanol/water, a total of 400 ml, was distilled off over a period of 4 hours. The remaining solution was stirred under reflux overnight. It was cooled to 55–60° C. and then an additional 37.5 g of conc. hydrochloric acid was added over a period of 5 min. The solution was cooled to 50–52° C. and was stirred at this temperature for 18 hours. The resulting precipitate was collected by filtration and was washed with 20 ml of water. The product was dried under vacuum at room temperature to give 40.5 g of Tiagabine, hydrochloride.

Yield: 86%.

K.F.: 0.4% water.

X-Ray: Complies with the anhydrous crystal form.

EXAMPLE 6

Tiagabine. hydrochloride (anhydrous)

To a 1 L flask, 50 g of tiagabine ethyl ester, 575 ml of water and 25 g of conc. hydrochloric acid were charged. The mixture was heated to reflux for 1 hour and then ethanol/water, a total of 200 ml, was distilled off over a period of 4 hours. The reaction solution was cooled to 88° C. and then an additional 23.5 g of conc. hydrochloric acid was added. The solution was gradually cooled to room temperature (22° C.) while the reaction was stirred for 18 hours. The resulting precipitate was collected by filtration and was washed with 20 ml of water. The product was dried under vacuum at room temperature to give 42.0 g of Tiagabine, hydrochloride.

Yield: 90%.

K.F.: 0.1% water.

X-Ray: Complies with the anhydrous crystal form.

What is claimed is:

1. Anhydrous crystalline R(−)-N-(4,4-di(3-methylthien-2yl)but-3-enyl)nipecotic acid hydrochloride having substantially the following X-ray powder diffraction peaks obtained with KBr: 6.4, 11.3, 13.0, 13.9, 15.0, 18.7, 19.4, 22.5 and 23.7.

2. Anhydrous crystalline R(−)-N-(4,4-di(3-methylthien-2yl)but-3-enyl)nipecotic acid hydrochloride substantially free of bound organic solvent and having substantially the following X-ray powder diffraction peaks obtained with KBr: 6.4, 11.3, 13.0, 13.9, 15.0, 18.7, 19.4, 22.5 and 23.7.

3. A process for the preparation of anhydrous crystalline R(−)-N-(4,4-di(3-methylthien-2yl)but-3-enyl)nipecotic acid hydrochloride having substantially the following X-ray powder diffraction peaks obtained with KBr: 6.4, 11.3, 13.0, 13.9, 15.0, 18.7, 19.4, 22.5 and 23.7 which process comprises a) dissolving tiagabine hydrochloride in an aqueous hydrochloric acid solution, and b) precipitating tiagabine hydrochloride from the aqueous hydrochloric acid solution.

4. A pharmaceutical composition comprising a therapeutically effective amount of a crystalline salt according to claim 1 together with a pharmaceutically acceptable carrier or diluent.

5. The pharmaceutical composition according to claim 4 in the form of a dosage unit containing about 1.0–1500 mg of the active ingredients.

6. A method of inhibiting GABA uptake in a mammal in need of such treatment comprising administering an effective amount of a crystalline salt according to claim 1.

7. A method of inhibiting GABA uptake in a mammal in need of such treatment comprising administering a pharmaceutical composition according to claim 4.

* * * * *